United States Patent
De Sapio et al.

(10) Patent No.: US 9,858,391 B2
(45) Date of Patent: Jan. 2, 2018

(54) METHOD AND SYSTEM FOR TUNING A MUSCULOSKELETAL MODEL

(71) Applicant: The Boeing Company, Chicago, IL (US)

(72) Inventors: Vincent De Sapio, Westlake Village, CA (US); Darren Earl, Pasadena, CA (US)

(73) Assignee: THE BOEING COMPANY, Chicago, IL (US)

( * ) Notice: Subject to any disclaimer, the term of this patent is extended or adjusted under 35 U.S.C. 154(b) by 213 days.

(21) Appl. No.: 14/502,478

(22) Filed: Sep. 30, 2014

(65) Prior Publication Data

US 2015/0302168 A1  Oct. 22, 2015

Related U.S. Application Data

(60) Provisional application No. 61/981,096, filed on Apr. 17, 2014.

(51) Int. Cl.
*G01N 33/48* (2006.01)
*G06F 19/00* (2011.01)
*G06G 7/58* (2006.01)

(52) U.S. Cl.
CPC ................................ *G06F 19/3437* (2013.01)

(58) Field of Classification Search
CPC .......... G06F 19/18; G06F 19/20; G06F 19/22; G06F 19/24; G01N 33/582
See application file for complete search history.

(56) References Cited

PUBLICATIONS

"Dunne et al., ""Tutorial 1—Intro to Musculoskeletal Modeling,""" Stanford University, OpenSim, last edited Jan. 2014, 8 pages, accessed Sep. 30, 2014.http://simtk-confluence.stanford.edu:8080/display/OpenSim/Tutorial+1+-+Intro+to+Musculoskeletal+Modeling".

Akagi et al, "Muscle volume compared to cross-sectional area is more appropriate for evaluating muscle strength in young and elderly individuals," Age and Ageing, Issue 38, Jul. 2009, pp. 564-569.

Delp et al., "OpenSim: Open-Source Software to Create and Analyze Dynamic Simulations of Movement," IEEE Transactions on Biomedical Engineering, vol. 54, No. 11, Nov. 2007, pp. 1940-1950.

Thelan et al., "Generating dynamic simulations of movement using computed muscle control," Journal of Biomechanics, vol. 36, Mar. 2003, pp. 321-328.

Thelan et al., "Using computed muscle control to generate forward dynamic simulations of human walking from experimental data," Journal of Biomechanics, vol. 39, copyright 2006, pp. 1107-1115.

Vidt et al., "Characterizing upper limb muscle volume and strength in older adults: A comparison with young adults," Journal of Biomechanics, vol. 45, Issue 2, Jan. 2012, pp. 334-341.

"Isometric Strength—Definition of Isometric Strength; Physical Strength Assessment in Ergonomics," Centers for Disease Control and Prevention, Jan. 1998, pp. 11-20.

Zajac, "Muscle Coordination of Movement: A Perspective," Journal of Biomechanics, vol. 26, Supplement 1, Feb. 1993, pp. 109-124.

*Primary Examiner* — Eric S Dejong
(74) *Attorney, Agent, or Firm* — Wonble Bond Dickinson (US) LLP (57) ABSTRACT

A computer-implemented method and system for modifying a musculoskeletal model is provided. Test data for a set of ergonomic tests performed by a number of test subjects fitting a profile is obtained. A number of muscle parameters for a number of muscles in the musculoskeletal model are adjusted using the test data to modify the musculoskeletal model to adapt to the profile.

18 Claims, 8 Drawing Sheets

METHOD AND SYSTEM FOR TUNING A MUSCULOSKELETAL MODEL

RELATED PROVISIONAL APPLICATION

This application claims the benefit of U.S. Provisional Patent Application Ser. No. 61/981,096, filed Apr. 17, 2014, and entitled "A Procedure for Tuning Generic Musculoskeletal Models to Specific Individual and Demographic Populations."

BACKGROUND INFORMATION

1. Field

The present disclosure relates generally to musculoskeletal models and, in particular, to modifying a musculoskeletal model. Still more particularly, the present disclosure relates to a method and system for tuning a musculoskeletal model to be adapted to a particular profile, such as a demographic profile.

2. Background

Biomechanical simulation has become increasingly important in domains such as, for example, without limitation, human factors engineering, clinical medicine, sports medicine, veterinary medicine, clinical biomechanics, clinical research, computer animation, rehabilitation research, biomedical engineering, and other such domains.

Human factors engineering is the practice of designing products, systems, or processes to take into account the interaction between these products, systems, or processes with the humans that use them. Human factors engineering may be relevant to fulfilling the goals of health, safety, and productivity in design. For example, human factors engineering, which may also be referred to as human factors and ergonomics, may include the designing of devices that fit the human body or that the human body otherwise uses. Proper ergonomic design of these devices may be important to preventing repetitive strain injuries, musculoskeletal disorders, and other types of medical issues. Human factors engineering may take into account the capabilities and limitations of a person to ensure that what is being designed suits that person.

Typically, biomechanical simulation involves running simulations using a computer model of the musculoskeletal system of a subject, such as a human or animal. A musculoskeletal model may consist of rigid body segments connected by joints and muscles that span these joints and that generate forces and movement. A musculoskeletal model may be used to study the forces and joint moments that the muscles can produce.

However, the musculoskeletal models that are often used for biomechanical simulations are generic models. For example, these models may represent an ideal or nominal subject, such as a 25-year-old male at the $50^{th}$ percentile with respect to a plurality of demographic factors. Simulations that are run using these types of generic musculoskeletal models may not provide accurate results for demographic profiles that fall outside the ideal or nominal demographic profile.

Currently available methods for correcting inaccuracies and errors in simulations run using generic musculoskeletal models or for adjusting generic musculoskeletal models may be significantly more time-consuming and expensive than desired. As one example, expensive medical imaging equipment and subsequent imaging data processing may be used to determine muscle volume loss in certain medical patients such that a musculoskeletal model may be modified. However, this process may be more time-consuming and expensive than desired and, in some cases, prohibitively expensive. Therefore, it would be desirable to have a method and apparatus that take into account at least some of the issues discussed above, as well as other possible issues.

SUMMARY

In one illustrative example, a computer-implemented method for modifying a musculoskeletal model is provided. Test data for a set of ergonomic tests performed by a number of test subjects fitting a profile is obtained. A number of muscle parameters for a number of muscles in the musculoskeletal model are adjusted using the test data to modify the musculoskeletal model to adapt to the profile.

In another illustrative example, a model management system comprises a simulator and a model modifier. The simulator obtains test data for a set of ergonomic tests performed by a number of test subjects fitting a profile and performs simulations using the test data and a musculoskeletal model. The model modifier adjusts a number of muscle parameters for a number of muscles in the musculoskeletal model based on the simulations to modify the musculoskeletal model to adapt to the profile.

In yet another illustrative example, a method for designing a product configured for a number of subjects that fit a profile is provided. A musculoskeletal model is modified based on simulations performed using the musculoskeletal model and test data for a set of ergonomic tests performed by a number of test subjects fitting the profile to generate a tuned musculoskeletal model. Biomechanical simulations are performed using the tuned musculoskeletal model to generate information for use in designing the product such that the product is adapted to the number of subjects that fit the profile.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative embodiments recognize and take into account different considerations. For example, the illustrative embodiments recognize and take into account that it may be desirable to perform biomechanical simulations using a musculoskeletal model that has been modified, or "tuned," to a particular subject profile. Tuning a musculoskeletal model to a particular subject profile means modifying the musculoskeletal model such that the musculoskeletal model may represent any subject that fits the particular subject profile within selected tolerances.

The subject profile may be comprised of values for a set of factors of interest that correspond to a particular subject or group of subjects. As one illustrative example, the illustrative embodiments recognize and take into account that it may be desirable to use a musculoskeletal model that has been adapted to a particular demographic profile for a particular subject or group of subjects.

Further, it may be desirable to have the capability of rapidly and autonomously modifying musculoskeletal models for individual subjects or demographic subject groups without needing to use expensive imaging equipment and imaging data processing to determine what modifications are needed. The illustrative embodiments recognize and take into account that isometric strength test data obtained by performing standard ergonomic experiments may be used to modify muscle parameters in musculoskeletal models. For example, isometric strength test data obtained from a particular subject or demographic subject group performing standard ergonomic experiments may be used to modify a musculoskeletal model to have subject-tuned or demographically-tuned muscle parameters.

Thus, the illustrative embodiments provide a method, apparatus, and system for rapidly and autonomously modifying a generic musculoskeletal model such that the muscle parameters of the musculoskeletal model are specifically adapted to a particular subject or subject group. As one illustrative example, test data for a set of ergonomic tests performed by a number of test subjects that fit a particular profile may be obtained. The particular profile may be comprised of a set of factors of interest. The particular profile may be, for example, without limitation, a demographic profile comprised of a set of demographic factors.

The test data obtained may be used to adjust a number of muscle parameters for a number of muscles in the musculoskeletal model to adapt the musculoskeletal model to the particular profile. In this manner, the musculoskeletal model may be tuned to represent a subject that fits the particular profile. The number of muscle parameters adjusted may include, for example, a strength parameter for each of the number of muscles. The strength parameter for a muscle may be, for example, without limitation, a maximum force limit for that muscle. The maximum force limit may be the maximum isometric force capable of being exerted by that muscle.

Thus, the illustrative embodiments provide a method and apparatus for modifying a musculoskeletal model based on test data for a set of ergonomic tests to generate a tuned musculoskeletal model that is adapted to a profile, such as a demographic profile. Biomechanical simulations may be performed using this tuned musculoskeletal model to, for example, without limitation, generate information for use in designing a product such that the product is adapted to a number of subjects that fit the profile. In this manner, the product may be designed such that the product takes into account that subjects fitting the profile will be using the product, is tailored for use by subjects who fit the profile, or both.

As one illustrative example, an overhead bin for an aircraft may need to be designed such that the overhead bin may be able to be used by persons who are elderly, have a disability, or deviate in some other manner from the typical average male or typical average female. By generating a tuned musculoskeletal model that is specifically adapted to subjects who fit these types of profiles, biomechanical simulations of a person using an overhead bin that are performed using the tuned musculoskeletal model may more accurately reflect how a person that fits these types of profiles would operate the overhead bin. Consequently, the information generated by these biomechanical simulations may be used to more accurately design the overhead bin. In this manner, the overall quality of the overhead bin may be improved.

Figure 1:
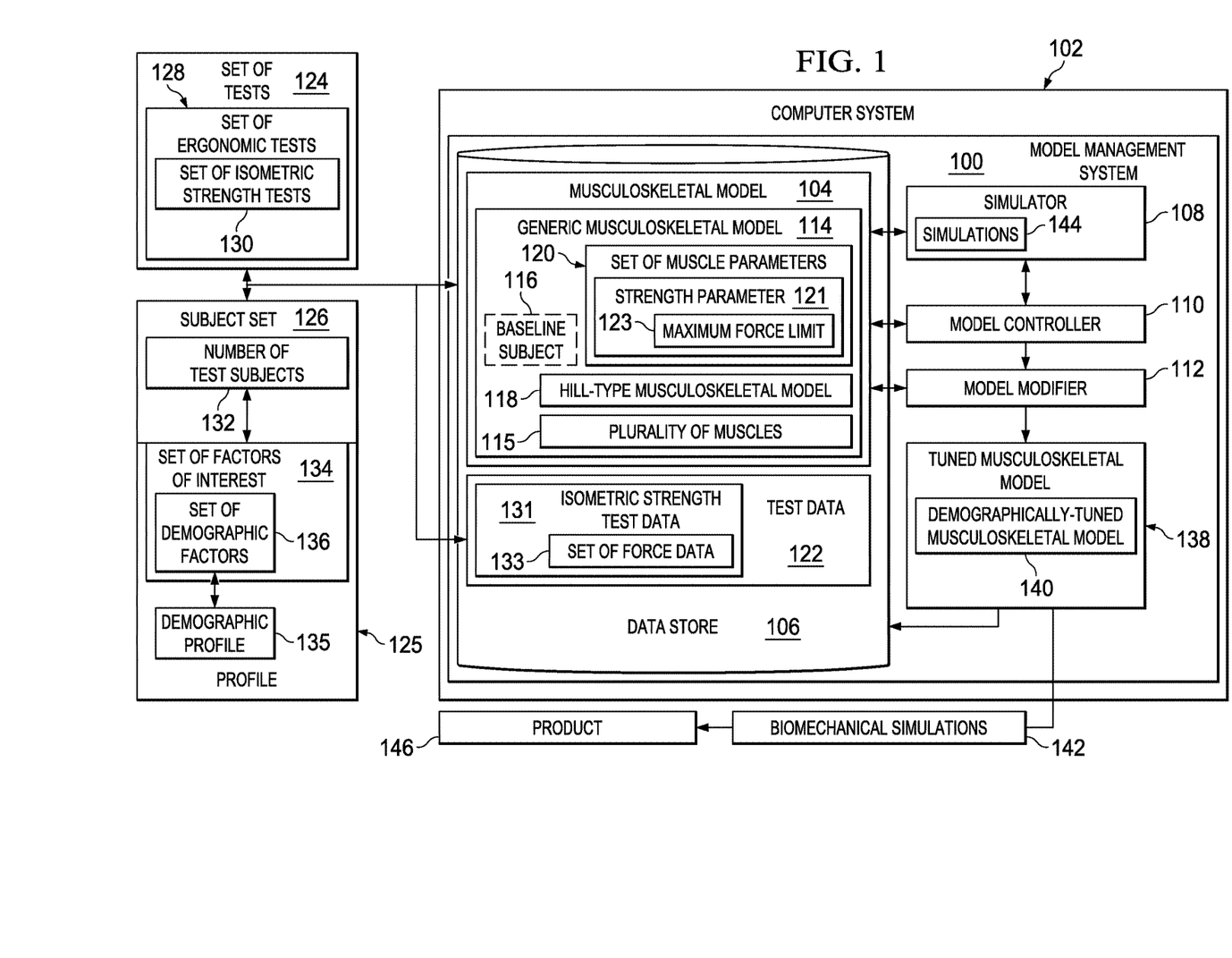
FIG. 1 is an illustration of a model management system in the form of a block diagram in accordance with an illustrative embodiment.

Referring now to the figures and, in particular, with reference to FIG. 1, an illustration of a model management system is depicted in the form of a block diagram in accordance with an illustrative embodiment. In this illustrative example, model management system 100 may be an example of a system that may be used to modify, or "tune" musculoskeletal model 104.

In this illustrative example, model management system 100 may be implemented in software, hardware, firmware, or a combination thereof. When software is used, the operations performed by model management system 100 may be implemented using, for example, without limitation, program code configured to run on a processor unit. When firmware is used, the operations performed by model management system 100 may be implemented using, for example, without limitation, program code and data and stored in persistent memory to run on a processor unit.

When hardware is employed, the hardware may include one or more circuits that operate to perform the operations performed by model management system 100. Depending on the implementation, the hardware may take the form of a circuit system, an integrated circuit, an application specific integrated circuit (ASIC), a programmable logic device, or some other suitable type of hardware device configured to perform any number of operations.

A programmable logic device may be configured to perform certain operations. The device may be permanently configured to perform these operations or may be reconfigurable. A programmable logic device may take the form of, for example, without limitation, a programmable logic array, a programmable array logic, a field programmable logic array, a field programmable gate array, or some other type of programmable hardware device.

In some illustrative examples, the operations and processes performed by model management system 100 may be performed using organic components integrated with inorganic components. In some cases, the operations and processes may be performed by entirely organic components, excluding a human being. As one illustrative example, circuits in organic semiconductors may be used to perform these operations and processes.

As depicted in this example, model management system 100 may be implemented in computer system 102. Computer system 102 may be comprised of one or more computers that may be in communication with each other.

Model management system 100 may include data store 106, simulator 108, model controller 110, and model modifier 112. Depending on the implementation, each of simulator 108, model controller 110, and model modifier 112 may be implemented using hardware, software, firmware, or a combination thereof.

Each of simulator 108, model controller 110, and model modifier 112 may be configured to access and interact with data store 106. Data store 106 may be comprised of at least one of a database, a data repository, a file, a flat file, a spreadsheet, a file system, an email storage system, or some other type of data storage.

As used herein, the phrase "at least one of," when used with a list of items, means different combinations of one or more of the listed items may be used and only one of the items in the list may be needed. The item may be a particular object, thing, action, process, or category. In other words, "at least one of" means any combination of items or number of items may be used from the list, but not all of the items in the list may be required.

For example, "at least one of item A, item B, or item C" or "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

In one illustrative example, musculoskeletal model 104 may be stored in data store 106. Musculoskeletal model 104 may represent the musculoskeletal structure of a subject. In particular, musculoskeletal model 104 may include plurality of muscles 115 that span joints connecting rigid body segments and that generate forces and movement.

As depicted, musculoskeletal model 104 may take the form of generic musculoskeletal model 114. Generic musculoskeletal model 114 may represent the musculoskeletal structure of baseline subject 116. Depending on the implementation, baseline subject 116 may be a human or an animal. In one illustrative example, baseline subject 116 may be a living subject. The living subject may be, for example, without limitation, a subject that was scanned, imaged, or tested in some other manner such that musculoskeletal model 104 is created to represent the living subject with a desired level of accuracy.

In another illustrative example, baseline subject 116 may be a nominal subject. A nominal subject may be a subject that exists in "name only" and that is not a currently living or previously living subject. A nominal subject may be considered a hypothetical subject or a theoretical subject in some cases. A nominal subject may be identified based on one or more average characteristics, median characteristics, ideal characteristics, or other types of characteristics. As one illustrative example, the nominal subject may be a 25-year-old male at the $50^{th}$ percentile with respect to one or more demographic factors.

In one illustrative example, musculoskeletal model 104 takes the form of Hill-type musculoskeletal model 118. Hill-type musculoskeletal model 118 may be a primarily mechanical musculoskeletal model based on the equations and theories formulated by Archibald Hill.

As depicted, each of plurality of muscles 115 may have set of muscle parameters 120. As used herein, a "set of" items may include one or more items. In this manner, set of muscle parameters 120 may include one or more muscle parameters.

Strength parameter 121 may be an example of one of set of muscle parameters 120. Strength parameter 121 may be, for example, without limitation, maximum force limit 123. Maximum force limit 123 for a corresponding muscle may be a maximum isometric force capable of being exerted by the corresponding muscle. In other words, maximum force limit 123 may define the maximum isometric strength of the corresponding muscle.

In other illustrative examples, set of muscle parameters 120 may include one or more other parameters in addition to or in place of strength parameter 121. For example, in some cases, set of muscle parameters 120 may include a muscle reaction time, joint moments, some other type of parameter, or some combination thereof.

Model management system 100 may be used to modify musculoskeletal model 104 to adapt musculoskeletal model 104 to a particular profile 125. Profile 125 may be a profile for a subject that is comprised of set of factors of interest 134. In one illustrative example, set of factors of interest 134 includes set of demographic factors 136. When set of factors of interest 134 only includes set of demographic factors 136, profile 125 may be referred to as a particular demographic profile 135. Set of demographic factors 136 may include at least one of, for example, without limitation, age, ethnicity, height, weight, income level, a disability, eye color, body type, body shape, occupation, location of residence, or some other type of demographic factor.

In other illustrative examples, set of factors of interest 134 may include one or more other factors in addition to or in place of set of demographic factors 136. These one or more other factors may include, for example, without limitation, at least one of a phenotype, a genotype, a characteristic, a feature, a medical condition, a sport, or some other type of factor of interest.

As one illustrative example, set of factors of interest 134 for profile 125 may include age. Musculoskeletal model 104 may then be modified to represent a subject of a particular age or within a particular age range.

Profile 125 may include a value, a range of values, or a category of values, for each of set of factors of interest 134. As used herein, a value for a factor of interest may take the form of a numerical value, a type, a variable, an alphanumeric string, or some other type of value.

In order to adapt musculoskeletal model 104 to profile 125, model management system 100 may obtain test data 122 corresponding to profile 125. Test data 122 may be associated with set of tests 124 performed by subject set 126 fitting profile 125. Subject set 126 may include number of test subjects 132. In this manner, test data 122 may be for set of tests 124 performed by number of test subjects 132 fitting profile 125. As used herein, a "number of" items may include one or more items. In this manner, number of test subjects 132 may include a single test subject or a plurality of test subjects.

In this illustrative example, set of tests 124 may include set of ergonomic tests 128. Set of ergonomic tests 128 may take the form of, for example, without limitation, a set of standard ergonomic exercises designed to test muscle strength. For example, set of ergonomic tests 128 may take the form of set of isometric strength tests 130. When set of ergonomic tests 128 takes the form of set of isometric strength tests 130, test data 122 may be referred to as isometric strength test data 131.

As used herein, an "isometric strength test," such as one of set of isometric strength tests 130, may be a test in which the capacity to produce a force or moment with voluntary isometric contraction is measured. With this type of test, one or more muscles may be activated. Further, with isometric contraction, these one or more muscles may maintain a substantially constant muscle length. In other words, the lengths of the muscle fibers in these muscles may remain substantially constant.

In this manner, no body movement should occur during an isometric strength test. In other words, the posture of the subject should remain substantially constant throughout the isometric strength test. The posture of a subject may include the orientation of the body of the subject and the various body angles of the subject. These body angles may include, for example, without limitation, the angles of the head, neck, trunk, limbs, extremities, and other members of the body relative to each other.

Each of set of ergonomic tests 128 may be associated with a corresponding set of test conditions. The set of test conditions for a particular test may include at least one of, for example, without limitation, an initial posture for the subject, a posture to be maintained by the subject throughout the test, an external force to be applied to the subject, a torque to be applied to the subject, a moment to be applied to the subject, or some other type of test condition. Under the corresponding set of test conditions for a particular ergonomic test, a strength measurement may be made and at least one of force data, moment data, or torque data may be generated based on this strength measurement. In this manner, isometric strength test data 131 may include set of force data 133 for set of tests 124.

Test data 122 may be stored in data store 106. Depending on the implementation, test data 122 may also be referred to as experimental data or exercise data. At least one of simulator 108 and model controller 110 may be capable of accessing and retrieving test data 122. Test data 122 may be used to modify musculoskeletal model 104 to generate tuned musculoskeletal model 138 that is adapted to the particular profile 125. When profile 125 takes the form of demographic profile 135, tuned musculoskeletal model 138 may be referred to as demographically-tuned musculoskeletal model 140. An example of one manner in which simulator 108, model controller 110, and model modifier 112 may modify musculoskeletal model 104 using test data 122 is described in FIG. 2 below.

In addition to test data 122, other types of test data may be stored in data store 106. For example, test data for other types of tests performed by other subjects fitting a demographic profile different from demographic profile 135 may be stored in data store 106. Test data for any number of tests performed by any number of test subjects corresponding to any number of profiles may be stored in data store 106.

Test data 122 stored in data store 106 may be obtained in any number of different ways. Test data 122 may be historical data or experimental data that may be retrieved from some other type of database for storage in data store 106. In other illustrative examples, test data 122 may be generated specifically for tuning musculoskeletal model 104. For example, number of test subjects 132 for performing set of tests 124 may be selected specifically based on profile 125 such that test data 122 corresponding to profile 125 may be obtained. Of course, in other illustrative examples, test data 122 may be obtained in some other manner.

Simulator 108 may perform simulations 144 using musculoskeletal model 104 based on set of test data 122 for set of ergonomic tests 128. Model controller 110 may control musculoskeletal model 104 during simulations 144. Model modifier 112 may adjust a number of muscle parameters for a number of muscles in musculoskeletal model 104 based on simulations 144 to modify musculoskeletal model 104 to adapt to profile 125 to generate tuned musculoskeletal model 104. Using test data 122 for set of ergonomic tests 128 may reduce at least one of a time, an expense, or a number of processing resources needed to adapt musculoskeletal model to profile 125.

Model management system 100 may be capable of rapidly and autonomously modifying musculoskeletal model 104 any number of times to generate any number of tuned musculoskeletal models. Significant time and cost savings may be obtained using these tuned musculoskeletal models to perform biomechanical simulations for domains such as, for example, human factors engineering. Further, using tuned musculoskeletal models may improve the accuracy with which these biomechanical simulations may be performed. Still further, using tuned musculoskeletal models may enable human factors engineering to be tailored to subjects fitting different types of profiles.

As one illustrative example, biomechanical simulations 142 may be performed using tuned musculoskeletal model 138 to generate information for use in designing product 146 such that product is adapted to a number of subjects that fit profile 125. Product 146 may take a number of different forms. For example, without limitation, product 146 may take the form of an ergonomic seat for a vehicle such as a ground vehicle, aerospace vehicle, water vehicle, or other type of vehicle. In other examples, product 146 may take the form of an overhead bin, a restraint device, a spacesuit, a door, a vacuum door, a steering wheel, a diving suit, or some other type of product.

Product 146 may take the form of any product that may need to be adapted to one or more subjects that do not fit the same profile as baseline subject 116. These subjects may include, for example, without limitation, the elderly, subjects with certain types of disabilities, athletes, bodybuilders, children, infants, females, subjects that fit some other type of profile 125.

Using test data 122 for set of ergonomic tests 128 may reduce at least one of a time, an expense, or a number of processing resources needed to adapt musculoskeletal model 104 to profile 125 to generate tuned musculoskeletal model 138 and at least one of a time, an expense, or a number of processing resources needed to design product 146 to the number of subjects that fit profile 146. In particular, using tuned musculoskeletal model 138 may improve the accuracy and quality with which product 146 is designed and manufactured.

Figure 2:
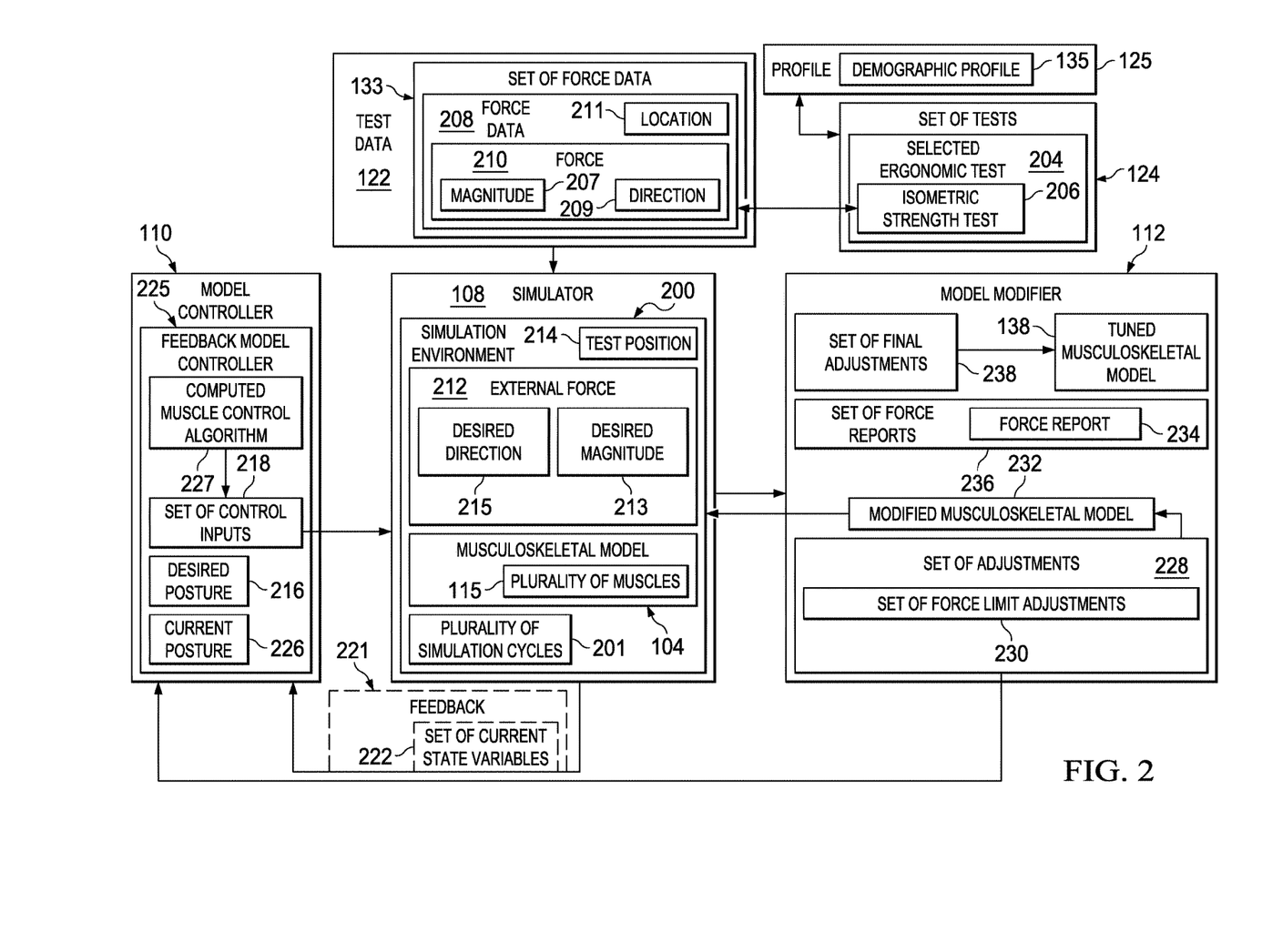
FIG. 2 is an illustration of a simulator, a model controller, and a model modifier in the form of a block diagram in accordance with an illustrative embodiment.

Turning now to FIG. 2, an illustration of simulator 108, model controller 110, and model modifier 112 from FIG. 1 is depicted in the form of a block diagram in accordance with an illustrative embodiment. In this illustrative example, simulator 108, model controller 110, and model modifier 112 may be used to modify musculoskeletal model 104 to generate tuned musculoskeletal model 138 that is adapted to profile 125.

In particular, simulator 108 may create simulation environment 200 for use in modifying musculoskeletal model 104. Simulation environment 200 may be created using, for example, without limitation, OpenSim, which is a freely available, open-source software system that allows users to build, exchange, and analyze musculoskeletal models and dynamic simulations of movement.

As depicted, simulator 108 may obtain test data 122 for set of tests 124 performed by number of test subjects 132 in FIG. 1 that fit profile 125. Simulator 108 may run plurality of simulation cycles 201 for each of set of tests 124 in simulation environment 200.

Selected ergonomic test 204 may be an example of a test selected from one of set of tests 124 that take the form of set of ergonomic tests 128 in FIG. 1. In other words, selected ergonomic test 204 may be selected from set of tests 124 in the form of ergonomic tests 128 in FIG. 1. Selected ergonomic test 204 may take the form of isometric strength test 206 in this example. Isometric strength test 206 may be an example of one of set of isometric strength tests 130 in FIG. 1.

Set of force data 133 in test data 122 may include force data 208 for isometric strength test 206. In this illustrative example, force data 208 may include, but is not limited to, magnitude 207, direction 209, and location 211 of force 210 generated by number of test subjects 132 in FIG. 1 for isometric strength test 206. Location 211 of force 210 may be a location with respect to the body of number of test subjects 132 in FIG. 1. When number of test subjects 132 includes multiple test subjects, magnitude 207, direction 209, and location 211 of force 210 may be, for example, without limitation, the average, median, or mode for the magnitude, direction, and location of the forces exerted by multiple test subjects in performing isometric strength test 206.

For isometric strength test 206, simulator 108 may identify desired magnitude 213 and desired direction 215 for external force 212. Desired magnitude 213 may be selected as being substantially equal to magnitude 207 of force 210. However, desired direction 215 may be selected as being substantially opposite to direction 209 of force 210.

Within simulation environment 200, simulator 108 may apply external force 212 to test position 214 on musculoskeletal model 104. Test position 214 may be based on location 211 of force 210.

In this illustrative example, simulator 108 may apply external force 212 of desired magnitude 213 and having desired direction 215 at test position 214 on musculoskeletal model 104 over the span of plurality of simulation cycles 201 to allow musculoskeletal model 104 to stabilize to external force 212 of desired magnitude 213. Musculoskeletal model 104 may be considered as stabilizing to external force 212 of desired magnitude 213 and having desired direction 215 when musculoskeletal model 104 is able to maintain desired posture 216 during at least one entire simulation cycle. Desired posture 216 may be substantially equal to the posture maintained by number of test subjects 132 during isometric strength test 206. In this manner, stabilizing musculoskeletal model 104 to external force 212 within simulation environment 200 may effectively be a simulation of isometric strength test 206.

In some cases, simulator 108 may immediately apply external force 212 of desired magnitude 213 and having desired direction 215 at test position 214 on musculoskeletal model 104. In other illustrative examples, simulator 108 may run multiple simulation cycles in order to increase external force 212 from a magnitude of substantially zero or some other minimum magnitude to desired magnitude 213. As one specific example, simulator 108 may linearly increase external force 212 from a magnitude of substantially zero to desired magnitude 213 over 10, 20, 30, 90, or some other number of simulation cycles.

Model controller 110 is configured to control musculoskeletal model 104 in simulation environment 200 such that musculoskeletal model 104 maintains desired posture 216 during the application of external force 212 at test position 214. In particular, model controller 110 may generate set of control inputs 218 for each of plurality of muscles 115. Set of control inputs 218 for each of plurality of muscles 115 may be used to control musculoskeletal model 104 such that musculoskeletal model 104 maintains desired posture 216. Set of control inputs 218 may represent neural excitations to the corresponding muscle.

In this illustrative example, set of control inputs 218 for a corresponding one of plurality of muscles 115 may include at least one excitation input for the corresponding muscle. The excitation input for the corresponding muscle may be, for example, without limitation, a percentage of maximum force limit 123, as described in FIG. 1, for the corresponding muscle.

Model controller 110 may use feedback control to adjust set of control inputs 218 for at least a portion of plurality of muscles 115 to try to maintain desired posture 216 substantially constant during the application of external force 212 at test position 214. For example, for each simulation cycle run by simulator 108, simulator 108 may generate feedback 221 that is sent to model controller 110, which may use feedback 221 to adjust set of control inputs 218 for at least a portion of plurality of muscles 115 to compensate for external force 212. Feedback 221 may include set of current state variables 222 for each of plurality of muscles 115 in musculoskeletal model 104.

As one illustrative example, model controller 110 may receive set of current state variables 222 after one simulation cycle has been run. Model controller 110 may compute current posture 226 of musculoskeletal model 104 in simulation environment 200 based on set of current state variables 222. Model controller 110 may then determine whether current posture 226 of musculoskeletal model 104 in simulation environment 200 is equal to desired posture 216 within selected tolerances. If current posture 226 is not equal to desired posture 216 within selected tolerances, model controller 110 may adjust set of control inputs 218 for at least a portion of plurality of muscles 115 in musculoskeletal model 104 to adjust current posture 226 of musculoskeletal model 104 in simulation environment 200 to compensate for external force 212 and maintain desired posture 216. Model controller 110 may use, for example, computed muscle control algorithm 227 to adjust set of control inputs 218 for at least a portion of plurality of muscles 115.

In one illustrative example, set of current state variables 222 may include, but is not limited to, the following variables for each of plurality of muscles 115: activation, a; joint coordinates, q; joint velocity, v; and muscle fiber or muscle length, l. Model controller 110 may use these variables to compute current posture 226 and determine whether current posture 226 is substantially equal to desired posture 216.

Model controller 110 may then adjust set of control inputs 218 for at least a portion of plurality of muscles 115 using computed muscle control algorithm 227 such that when the adjusted set of control inputs 218 is received by musculoskeletal model 104 within simulation environment 200, current posture 226 is moved closer to desired posture 216. For example, adjusting set of control inputs 218 for at least a portion of plurality of muscles 115 may include increasing or decreasing the excitation input for one or more of plurality of muscles 115 in order to stabilize musculoskeletal model 104 to external force 212.

In this manner, model controller 110 may use feedback 221 to stabilize musculoskeletal model 104 to external force 212. In some illustrative examples, model controller 110 may be referred to as feedback model controller 225.

In some cases, musculoskeletal model 104 may be unable to stabilize to external force 212. In other words, musculoskeletal model 104 may be unable to maintain desired posture 216 without exceeding the maximum force limit of at least one of plurality of muscles 115. As one illustrative example, even with one or more of the excitation inputs at about 100 percent, musculoskeletal model 104 may be unable to maintain desired posture 216.

In these cases, model modifier 112 may compute set of adjustments 228 for at least a portion of plurality of muscles 115. As one illustrative example, set of adjustments 228 may include an increase in the maximum force limits for each of plurality of muscles 115. The increase may be, for example, without limitation, an increase by a selected value or an increase by a selected percentage. In this manner, when musculoskeletal model 104 is unable to maintain desired posture 216 during the entirety of at least one of plurality of simulation cycles 201 while external force 212 of desired magnitude 213 and having desired direction 215 is applied at test position 214, set of adjustments 228 may take the form of set of force limit adjustments 230 for use in changing the maximum force limits for all of plurality of muscles 115.

Once set of adjustments 228 have been computed, model modifier 112 may modify musculoskeletal model 104 using set of adjustments 228 to generate modified musculoskeletal model 232. Thereafter, the entire process of applying external force 212 of desired magnitude 213 and having desired direction 215 at test position 214 over plurality of simulation cycles 201 and using feedback control to try to maintain desired posture 216 is repeated using modified musculoskeletal model 232.

This overall process of running plurality of simulation cycles 201 and adjusting musculoskeletal model 104 may be performed iteratively until musculoskeletal model 104 is able to stabilize to external force 212 of desired magnitude 213 and having desired direction 215. Once stabilization has been reached, force report 234 may be created. Force report 234 may identify the final maximum force limit for each of plurality of muscles 115 in musculoskeletal model 104.

In some illustrative examples, musculoskeletal model 104 may be able to stabilize to external force 212 of desired magnitude 213 and having desired direction 215 the first time that plurality of simulation cycles 201 is run in correspondence with isometric strength test 206. In these examples, the maximum force limit for at least one of plurality of muscles 115 may need to be lowered such that the maximum force limits for plurality of muscles 115 are just at the threshold force limit needed in order for musculoskeletal model 104 to be able to stabilize to external force 212 of desired magnitude 213 and having desired direction 215 in correspondence with isometric strength test 206.

This entire process as performed for isometric strength test 206 may then be repeated for each of set of tests 124 starting with musculoskeletal model 104 in its original state. In this manner, set of force reports 236 may be generated corresponding to set of tests 124. Set of force reports 236 may be evaluated to select the greatest maximum force limit across set of force reports 236 for each of plurality of muscles 115 to establish set of final adjustments 238.

Set of final adjustments 130 may include an adjustment for each of a number of muscle parameters for each of a number of muscles selected from plurality of muscles 115 for musculoskeletal model 104. For example, the number of muscle parameters may be one or more of set of muscle parameters 120 in musculoskeletal model 104 for each of at least a portion of plurality of muscles 115. The at least a portion of plurality of muscles 115 may be one, some, or all of plurality of muscles 115, depending on the implementation. Musculoskeletal model 104 may then be modified using set of final adjustments 238 to generate tuned musculoskeletal model 138 that is adapted to profile 125.

In this manner, each of plurality of muscles 115 in tuned musculoskeletal model 138 may have maximum force limit 123 needed such that tuned musculoskeletal model 138 may be able to satisfactorily perform each of set of tests 124. In other words, tuned musculoskeletal model 138 may represent the musculoskeletal structure of a subject that fits profile 125.

With tuned musculoskeletal model 138, significant time and cost savings may be obtained using in designing, for example, product 146 that is configured for use by or with a subject that fits profile 125. As one illustrative example, biomechanical simulations 142 in FIG. 1 may be performed for domains such as, but not limited to, human factors engineering such that product 146 in FIG. 1 may be specifically designed for, or tailored to, subjects that fit profile 125.

The illustrations of model management system 100 in FIG. 1 and simulator 108, model controller 110, and model modifier 112 in FIGS. 1-2 are not meant to imply physical or architectural limitations to the manner in which an illustrative embodiment may be implemented. Other components in addition to or in place of the ones illustrated may be used. Some components may be optional. Also, the blocks are presented to illustrate some functional components. One or more of these blocks may be combined, divided, or combined and divided into different blocks when implemented in an illustrative embodiment.

Figure 3:
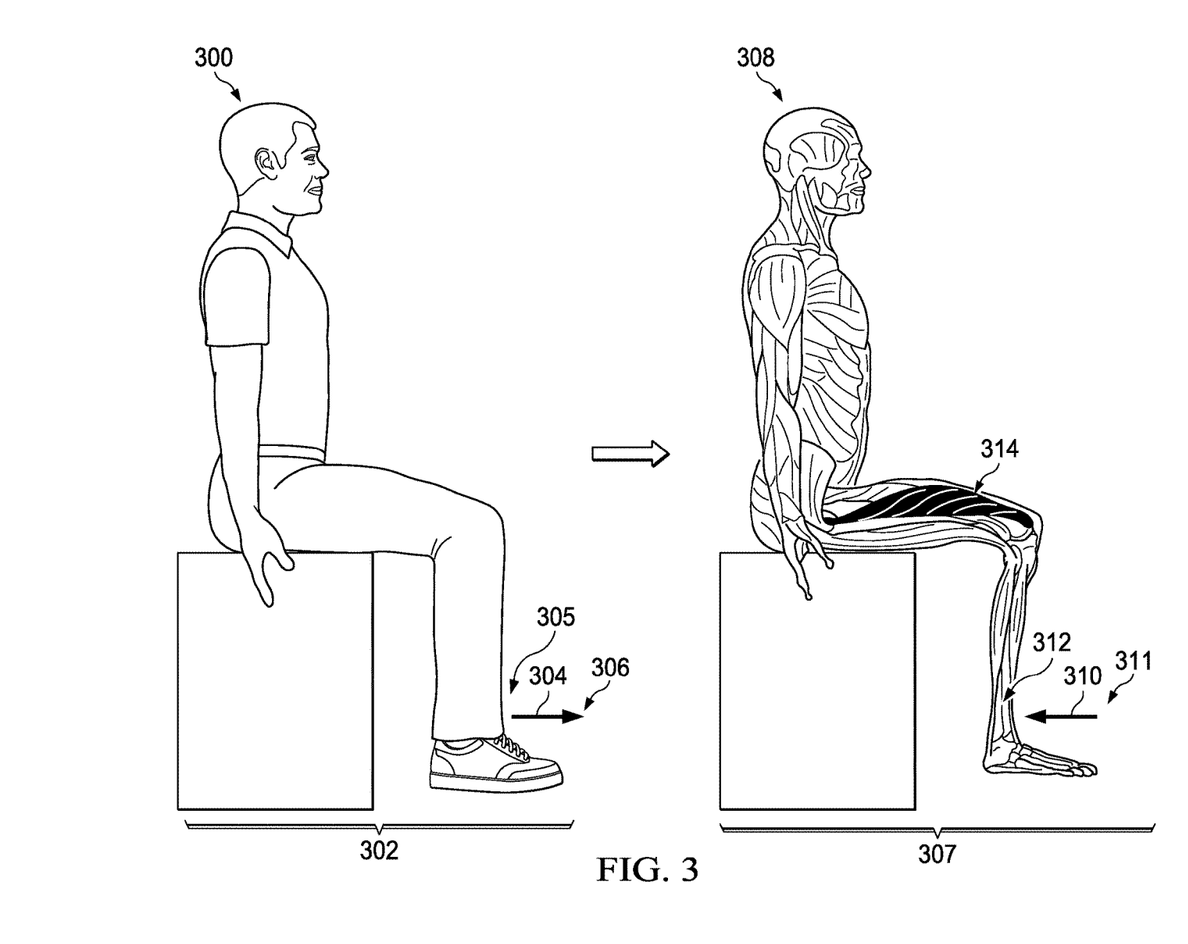
FIG. 3 is an illustration of an isometric strength test and a corresponding simulation in accordance with an illustrative embodiment.

With reference now to FIG. 3, an illustration of an isometric strength test and a corresponding simulation is depicted in accordance with an illustrative embodiment. In this illustrative example, test subject 300 performs isometric strength test 302. Test subject 300 may be a living subject in this example. Test subject 300 performing isometric strength test 302 may be an example of one implementation of one number of test subjects 123 performing one of set of isometric strength tests 130 in FIG. 1.

Isometric strength test 302 may be a knee extension test in this illustrative example. Isometric strength test 302 may be an example of one implementation for isometric strength test 206 in FIG. 2. Force 304 may be measured in correspondence with the isometric strength of test subject 300. Force 304 may have direction 306 and may be measured at location 305.

In this illustrative example, simulation 307 may be run using musculoskeletal model 308. Musculoskeletal model 308 may be an example of one implementation for musculoskeletal model described in FIGS. 1-2. External force 310 having direction 311 may be applied to test position 312 on musculoskeletal model 308 in correspondence with isometric strength test 302. External force 310 may have substantially the same magnitude as force 304. However, direction 311 of external force 310 may be opposite to direction 306 of force 304.

Test position 312 may be selected based on location 305. In this illustrative example, test position 312 is the same as location 305. Set of activated muscles 314 may be the muscles needed to respond to the application of external force 310.

Figure 4:
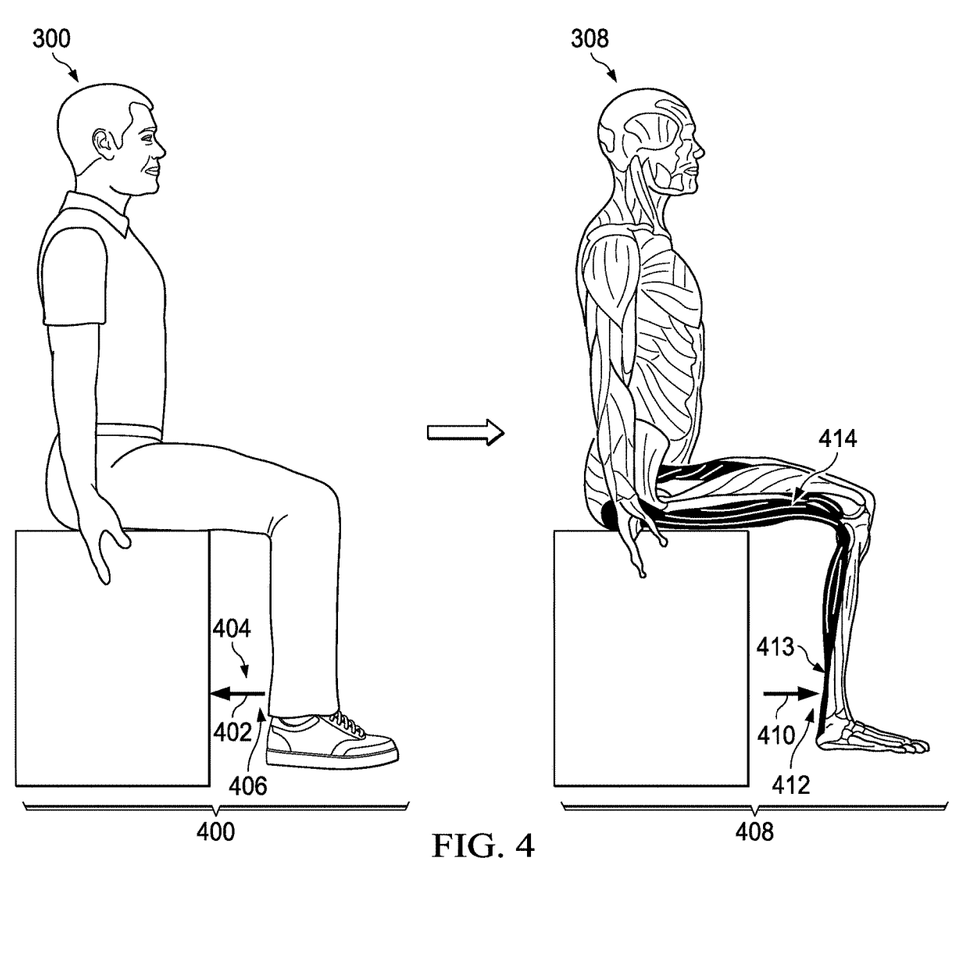
FIG. 4 is an illustration of an isometric strength test and a corresponding simulation in accordance with an illustrative embodiment.

With reference now to FIG. 4, an illustration of an isometric strength test and a corresponding simulation is depicted in accordance with an illustrative embodiment. In this illustrative example, test subject 300 from FIG. 3 performs isometric strength test 400. Test subject 300 performing isometric strength test 400 may be an example of one implementation of one number of test subjects 123 performing one of set of isometric strength tests 130 in FIG. 1.

Isometric strength test 400 may be a knee flexion test in this illustrative example. Isometric strength test 400 may be another example of one implementation for isometric strength test 206 in FIG. 2. Force 402 may be measured in correspondence with the isometric strength of test subject 300. Force 402 may have direction 404 and may be measured at location 406.

In this illustrative example, simulation 408 may be run using musculoskeletal model 308 from FIG. 3. External force 410 having direction 412 may be applied to test position 413 on musculoskeletal model 308 in correspondence with isometric strength test 400. External force 410 may have substantially the same magnitude as force 402. However, direction 412 of external force 410 may be opposite to direction 404 of force 402. Test position 413 may be selected based on location 406. In this illustrative example, test position 413 is the same as location 406. Set of activated muscles 414 may be the muscles needed to respond to the application of external force 410.

Figure 5:
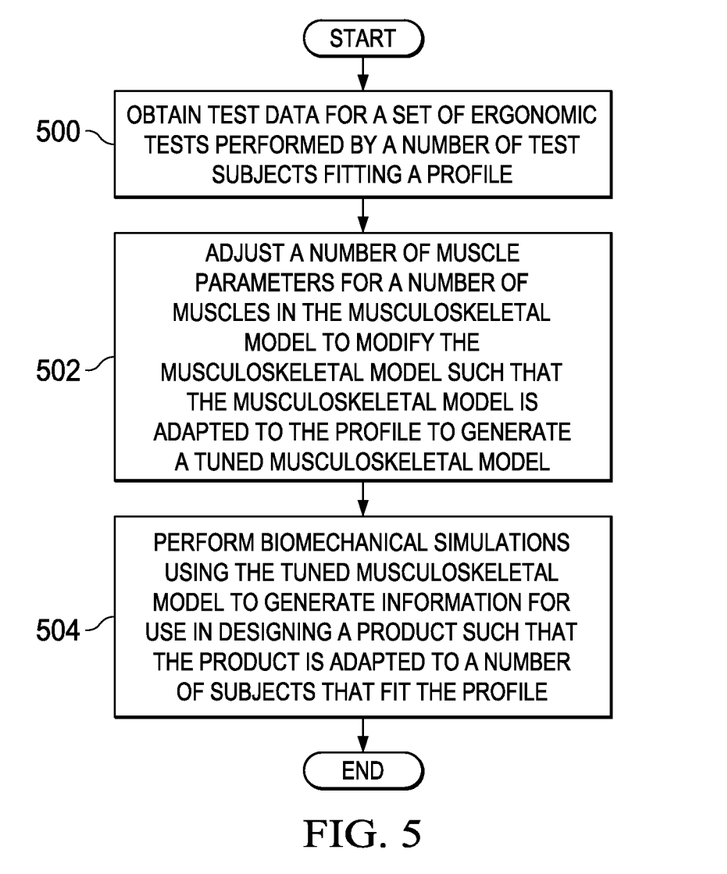
FIG. 5 is an illustration of a process for modifying a musculoskeletal model in the form of a flowchart in accordance with an illustrative embodiment.

With reference now to FIG. 5, an illustration of a process for modifying a musculoskeletal model is depicted in the form of a flowchart in accordance with an illustrative embodiment. The process illustrated in FIG. 5 may be implemented using model management system 100 in FIGS. 1-2.

The process may begin by obtaining test data for a set of ergonomic tests performed by a number of test subjects fitting a profile (operation 500). In one illustrative example, the profile may be a demographic profile. Next, a number of muscle parameters for a number of muscles in the musculoskeletal model are adjusted to modify the musculoskeletal model such that the musculoskeletal model is adapted to the profile to generate a tuned musculoskeletal model (operation 502).

In operation 502, the number of muscle parameters adjusted may be one or more of the set of muscle parameters in the musculoskeletal model for each of the number of muscles. For example, the number of muscle parameters adjusted may be one or more of set of muscle parameters 120 for each of a number of muscles from plurality of muscles 115. The number of muscles may be one, some, or all of plurality of muscles 115, depending on the implementation.

Next, biomechanical simulations may be performed using the tuned musculoskeletal model to generate information for use in designing a product such that the product is adapted to a number of subjects that fit the profile (operation 504), with the process terminating thereafter. Using the test data for the set of ergonomic tests reduces at least one of a time, an expense, or a number of processing resources needed to adapt the musculoskeletal model to the profile and to design the product to the number of subjects that fit the profile.

In other illustrative examples, operation 504 may be replaced with another operation that performs biomechanical simulations using the tuned musculoskeletal model to generate information for some other purpose or goal in the field of some other domain. This other domain may take the form of, for example, without limitation, human factors engineering, clinical medicine, sports medicine, veterinary medicine, clinical biomechanics, clinical research, computer animation, rehabilitation research, biomedical engineering, or some other suitable type of domain.

Figure 6:
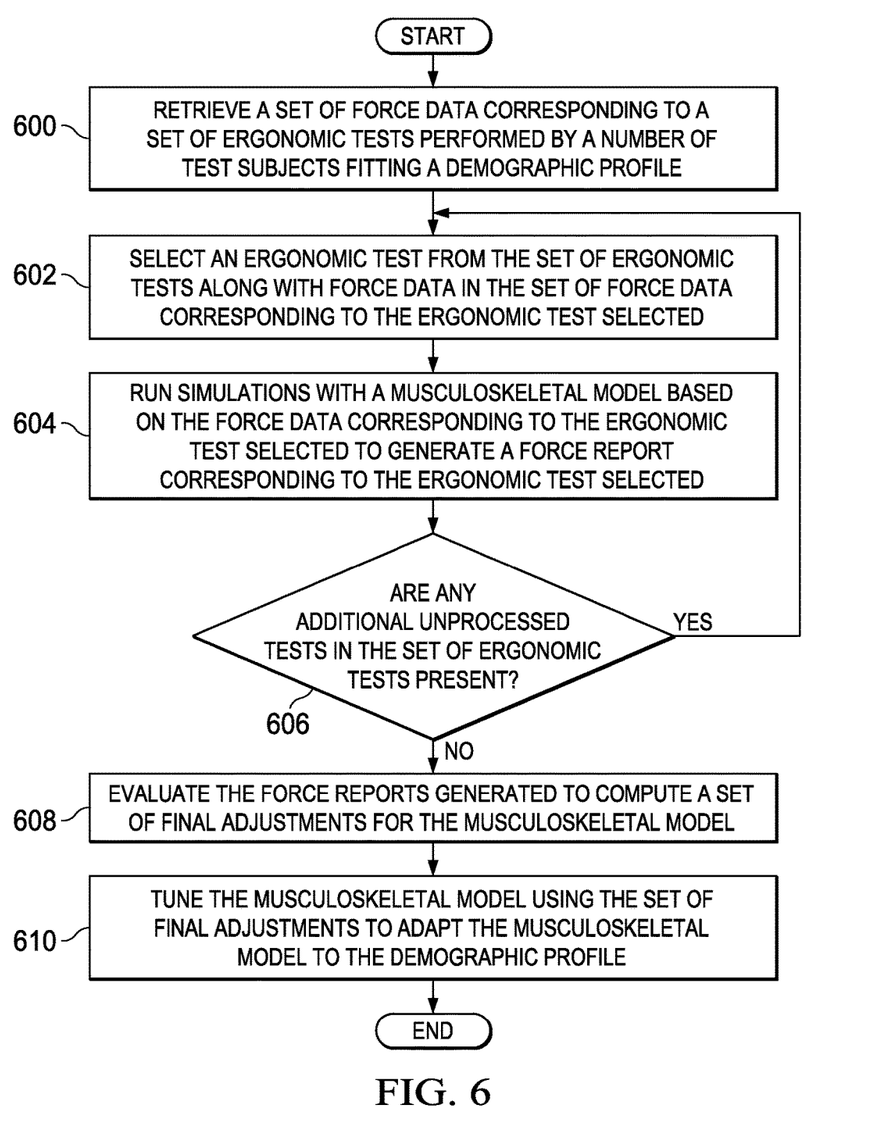
FIG. 6 is an illustration of a process for adapting a musculoskeletal model to a demographic profile in the form of a flowchart in accordance with an illustrative embodiment.

With reference now to FIG. 6, an illustration of a process for adapting a musculoskeletal model to a demographic profile is depicted in the form of a flowchart in accordance with an illustrative embodiment. The process illustrated in FIG. 6 may be implemented using model management system 100 in FIGS. 1-2.

The process may begin by retrieving a set of force data corresponding to a set of ergonomic tests performed by a number of test subjects fitting a demographic profile (operation 600). In operation 600, the set of force data may be retrieved from, for example, without limitation, a data store.

Next, an ergonomic test is selected from the set of ergonomic tests along with force data in the set of force data corresponding to the ergonomic test selected (operation 602). The force data includes a magnitude, a direction, and a location for a force measured for a number of test subjects in correspondence with the ergonomic test selected.

Thereafter, simulations with a musculoskeletal model are run based on the force data corresponding to the ergonomic test selected to generate a force report corresponding to the ergonomic test selected (operation 604). Thereafter, a determination is then made as to whether any additional unprocessed tests in the set of ergonomic tests are present (operation 606). If any unprocessed ergonomic tests are present, the process returns to operation 602 as described above. Otherwise, the force reports generated are evaluated to compute a set of final adjustments for the musculoskeletal model (operation 608). The musculoskeletal model is tuned using the set of final adjustments to adapt the musculoskeletal model to the demographic profile (operation 610), with the process terminating thereafter.

Figure 7:
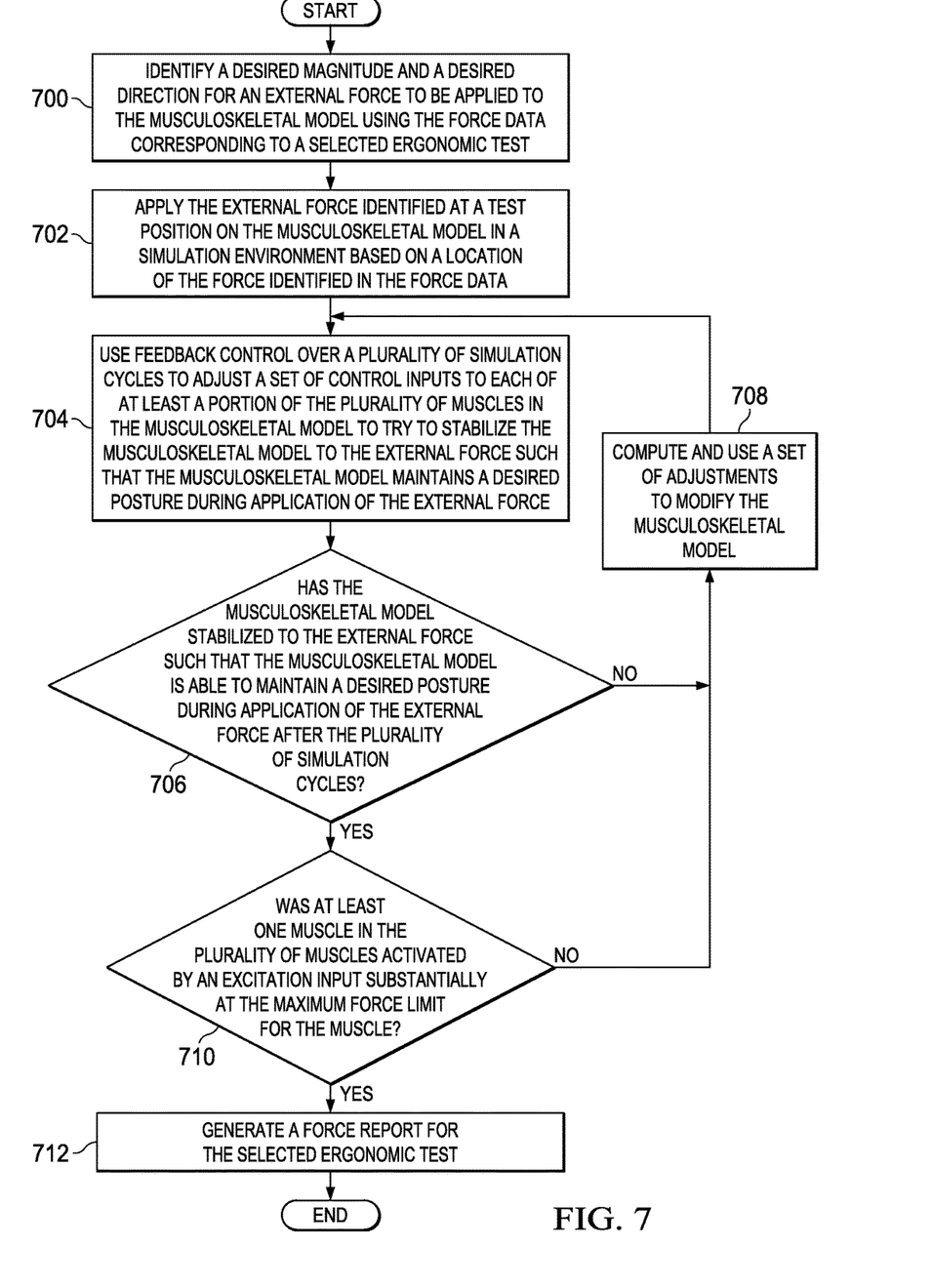
FIG. 7 is an illustration of a process for generating a force report in the form of a flowchart in accordance with an illustrative embodiment.

With reference now to FIG. 7, an illustration of a process for generating a force report is depicted in the form of a flowchart in accordance with an illustrative embodiment. The process illustrated in FIG. 7 may be an example of one manner in which operation 604 in FIG. 6 may be implemented.

The process begins by identifying a desired magnitude and a desired direction for an external force to be applied to the musculoskeletal model using the force data corresponding to a selected ergonomic test (operation 700). In operation 700, the desired magnitude may be substantially equal to a magnitude of a force identified in the force data. The desired direction may be opposite to a direction of the force identified in the force data.

Next, the external force identified is then applied at a test position on the musculoskeletal model in a simulation environment based on a location of the force identified in the force data (operation 702). Feedback control is used over a plurality of simulation cycles to adjust a set of control inputs to each of at least a portion of the plurality of muscles in the musculoskeletal model to try to stabilize the musculoskeletal model to the external force such that the musculoskeletal model maintains a desired posture during application of the external force (operation 704).

A determination is made as to whether the musculoskeletal model has stabilized to the external force such that the musculoskeletal model is able to maintain a desired posture during application of the external force after the plurality of simulation cycles (operation 706). If the musculoskeletal model is not able to maintain the desired posture after the plurality of simulation cycles, a set of adjustments are computed and used to modify the musculoskeletal model (operation 708), with the process then returning to operation 704 described above.

With reference again to operation 706, if the musculoskeletal model is able to maintain the desired posture, a determination is made as to whether at least one muscle in the plurality of muscles was activated by an excitation input substantially at the maximum force limit for the muscle (operation 710). If no muscles in the musculoskeletal model were activated by an excitation input substantially at the maximum force limit for the muscle, the process proceeds to operation 708 as described above. The set of adjustments made may lower the maximum force limits for all of the plurality of muscles in the musculoskeletal model.

With reference again to operation 710, if at least one muscle in the plurality of muscles was activated by an excitation input substantially at the maximum force limit for the muscle, the process generates a force report for the selected ergonomic test (operation 712), with the process terminating thereafter.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, a segment, a function, a portion of an operation or step, some combination thereof.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

Figure 8:
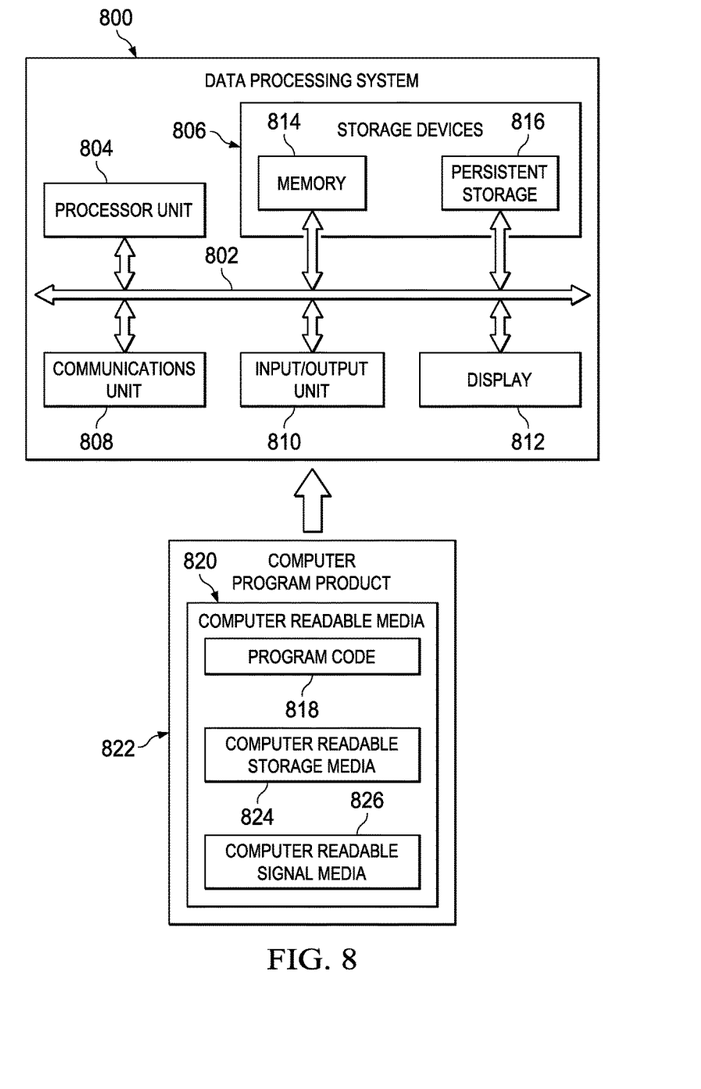
FIG. 8 is an illustration of a data processing system in the form of a block diagram in accordance with an illustrative embodiment.

Turning now to FIG. 8, an illustration of a data processing system is depicted in the form of a block diagram in accordance with an illustrative embodiment. Data processing system 800 may be used to implement computer system 102 in FIG. 1. As depicted, data processing system 800 includes communications framework 802, which provides communications between processor unit 804, storage devices 806, communications unit 808, input/output unit 810, and display 812. In some cases, communications framework 802 may be implemented as a bus system.

Processor unit 804 is configured to execute instructions for software to perform a number of operations. Processor unit 804 may comprise at least one of a number of processors, a multi-processor core, or some other type of processor, depending on the implementation. In some cases, processor unit 804 may take the form of a hardware unit, such as a circuit system, an application specific integrated circuit (ASIC), a programmable logic device, or some other suitable type of hardware unit.

Instructions for the operating system, applications and programs run by processor unit 804 may be located in storage devices 806. Storage devices 806 may be in communication with processor unit 804 through communications framework 802. As used herein, a storage device, also referred to as a computer readable storage device, is any piece of hardware capable of storing information on a temporary basis, a permanent basis, or both. This information may include, but is not limited to, data, program code, other information, or some combination thereof.

Memory 814 and persistent storage 816 are examples of storage devices 806. Memory 814 may take the form of, for example, a random access memory or some type of volatile or non-volatile storage device. Persistent storage 816 may comprise any number of components or devices. For example, persistent storage 816 may comprise a hard drive, a flash memory, a rewritable optical disk, a rewritable magnetic tape, or some combination of the above. The media used by persistent storage 816 may or may not be removable.

Communications unit 808 allows data processing system 800 to communicate with other data processing systems, devices, or both. Communications unit 808 may provide communications using physical communications links, wireless communications links, or both.

Input/output unit 810 allows input to be received from and output to be sent to other devices connected to data processing system 800. For example, input/output unit 810 may allow user input to be received through a keyboard, a mouse, some other type of input device, or a combination thereof. As another example, input/output unit 810 may allow output to be sent to a printer connected to data processing system 800.

Display 812 is configured to display information to a user. Display 812 may comprise, for example, without limitation, a monitor, a touch screen, a laser display, a holographic display, a virtual display device, some other type of display device, or a combination thereof.

In this illustrative example, the processes of the different illustrative embodiments may be performed by processor unit 804 using computer-implemented instructions. These instructions may be referred to as program code, computer usable program code, or computer readable program code and may be read and executed by one or more processors in processor unit 804.

In these examples, program code 818 is located in a functional form on computer readable media 820, which is selectively removable, and may be loaded onto or transferred to data processing system 800 for execution by processor unit 804. Program code 818 and computer readable media 820 together form computer program product 822. In this illustrative example, computer readable media 820 may be computer readable storage media 824 or computer readable signal media 826.

Computer readable storage media 824 is a physical or tangible storage device used to store program code 818 rather than a medium that propagates or transmits program code 818. Computer readable storage media 824 may be, for example, without limitation, an optical or magnetic disk or a persistent storage device that is connected to data processing system 800.

Alternatively, program code 818 may be transferred to data processing system 800 using computer readable signal media 826. Computer readable signal media 826 may be, for example, a propagated data signal containing program code 818. This data signal may be an electromagnetic signal, an optical signal, or some other type of signal that can be transmitted over physical communications links, wireless communications links, or both.

The illustration of data processing system 800 in FIG. 8 is not meant to provide architectural limitations to the manner in which the illustrative embodiments may be implemented. The different illustrative embodiments may be implemented in a data processing system that includes components in addition to or in place of those illustrated for data processing system 800. Further, components shown in FIG. 8 may be varied from the illustrative examples shown.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method comprising:
    determining a group of subjects fitting a demographic profile for whom a product is to be designed;
    determining at least one of a set of demographic factors representative of the group of subjects;
    determining a set of tests based on the at least one of the set of demographic factors, the set of tests facilitating simulations of subjects in the group of subjects using the product;
    conducting the determined set of tests, the determined set of tests including a set of force data for a set of ergonomic tests under a corresponding set of test conditions performed by multiple subjects;
    adjusting, by a computer system, a number of muscle parameters for a number of muscles in a musculoskeletal model to adapt to the demographic profile, wherein adjusting the number of muscle parameters comprises:
        generating a set of force reports corresponding to the set of ergonomic tests by performing simulations with the musculoskeletal model based on the set of force data for the set of ergonomic tests;
        computing a set of final adjustments using the set of force reports, wherein the set of final adjustments is established by selecting a greatest maximum force limit across the set of force reports for each of the number of muscles; and
        modifying the musculoskeletal model using the set of final adjustments to generate a tuned musculoskeletal model that is adapted to the demographic profile;
    performing, by the computer system, biomechanical simulations with the tuned musculoskeletal model to generate information for use in designing the product; and
    generating, using the information generated by the biomechanical simulations, a design of the product adapted to subjects that fit the profile.

2. The method of claim 1, wherein generating the set of force reports comprises:
    modifying the musculoskeletal model iteratively until the musculoskeletal model is stabilized to an external force applied at a test position on the musculoskeletal model based on force data corresponding to a selected ergonomic test from the set of ergonomic tests;
    generating a force report for the selected ergonomic test; and
    repeating the step of modifying the musculoskeletal model iteratively and generating the force report for the selected ergonomic test for each of a remaining portion of the set of ergonomic tests.

3. The method of claim 2, wherein modifying the musculoskeletal model iteratively comprises:
    identifying a magnitude, a direction, and a location of a force using the force data corresponding to the selected ergonomic test; and
    applying the external force at the test position on the musculoskeletal model over a plurality of simulation cycles, wherein the external force has a desired magnitude substantially equal to the magnitude of the force and a desired direction substantially opposite to the direction of the force and wherein the test position is based on the location of the force.

4. The method of claim 3, wherein modifying the musculoskeletal model iteratively further comprises:
    adjusting a set of control inputs to each of at least a portion of a plurality of muscles in the musculoskeletal model using feedback control to try to stabilize the musculoskeletal model to the external force over the plurality of simulation cycles such that the musculoskeletal model maintains a desired posture during application of the external force.

5. The method of claim 4, wherein adjusting the set of control inputs comprises:
    receiving a set of current state variables as feedback from running a simulation cycle in a simulation environment using the musculoskeletal model in which the external force is applied at the test position on the musculoskeletal model; and
    adjusting, iteratively, at least a portion of the set of control inputs based on the set of current state variables over the plurality of simulation cycles to try to stabilize the musculoskeletal model to the external force.

6. The method of claim 5, wherein adjusting, iteratively, the at least a portion of the set of control inputs comprises:
    determining whether the musculoskeletal model has maintained the desired posture;
    adjusting at least one excitation input to the plurality of muscles in the musculoskeletal model; and
    repeating the step of determining whether the musculoskeletal model has maintained the desired posture and adjusting the at least one excitation input to the plurality of muscles in the musculoskeletal model until a maximum force limit for at least one of the plurality of muscles is reached.

7. The method of claim 3, wherein modifying the musculoskeletal model iteratively further comprises:
    determining whether the musculoskeletal model has maintained the desired posture after the plurality of simulation cycles have been run;
    modifying the musculoskeletal model using a set of adjustments in response to a determination that the musculoskeletal model has not maintained the desired posture; and
    repeating the step of applying the external force at the test position on the musculoskeletal model over the plurality of simulation cycles.

8. The method of claim 7, wherein generating the force report comprises:
    generating the force report for the selected ergonomic test in response to a determination that the musculoskeletal model has maintained the desired posture after the plurality of simulation cycles have been run.

9. The method of claim 1, wherein obtaining the set of force data comprises:
    obtaining isometric strength test data for a set of isometric strength tests performed by a number of subjects fitting a demographic profile.

10. The method of claim 1, wherein the product is one of an ergonomic seat for a vehicle, an overhead bin, a restraint device, a spacesuit, a door, a vacuum door, a steering wheel, or a diving suit.

11. The method of claim 1 further comprising:
performing, by the multiple test subjects, a set of ergonomic tests wherein strength measurements are made under the corresponding set of test conditions for the set of ergonomic tests, wherein the set of ergonomic tests is more than one ergonomic test, and wherein the set of force data is based on the strength measurements.

12. The method of claim 1 further comprising:
manufacturing the product using the design.

13. A model management system comprising:
a simulator that performs simulations using a musculoskeletal model based on a set of force data for a set of ergonomic tests, the set of ergonomic tests having been performed by a number of test subjects fitting a demographic profile to obtain test data, the number of test subjects being identified as subjects for whom a product is to be designed, wherein the simulator applies an external force at a test position on the musculoskeletal model based on force data corresponding to a selected ergonomic test from the set of ergonomic tests;
a model controller that adjusts a set of control inputs to each of at least a portion of a plurality of muscles in the musculoskeletal model using feedback control to try to stabilize the musculoskeletal model to the external force over a plurality of simulation cycles such that the musculoskeletal model maintains a desired posture during application of the external force; and
a model modifier that adjusts a number of muscle parameters for a number of muscles in the musculoskeletal model based on the simulations to modify the musculoskeletal model to adapt to the demographic profile, wherein the model modifier generates a set of force reports based on the simulations, wherein the model modifier computes a set of final adjustments using the set of force reports and modifies the musculoskeletal model using the set of final adjustments to generate a tuned musculoskeletal model that represents a musculoskeletal structure of a subject that fits the demographic profile, wherein the simulator performs biomechanical simulations with the tuned musculoskeletal model to generate information for use in designing a product, and wherein a design of the product, adapted to the number of test subjects that fit the demographic profile, is generated using the information generated by the biomechanical simulations.

14. The model management system of claim 13, wherein the test data is isometric strength test data and the set of ergonomic tests is a set of isometric strength tests.

15. The model management system of claim 13, wherein the set of control inputs includes at least one excitation input for a corresponding muscle in the number of muscles.

16. The model management system of claim 15, wherein the at least one excitation input is a percentage of a maximum force limit for the corresponding muscle.

17. The model management system of claim 13, wherein performing biomechanical simulations with the tuned musculoskeletal model comprises performing biomechanical simulations of a person using the product using the tuned musculoskeletal model, and wherein biomechanical simulations using the tuned musculoskeletal model more accurately reflects how a person fitting the demographic profile would use the product than the musculoskeletal model.

18. The model management system of claim 17, wherein the product is one of an ergonomic seat for a vehicle, an overhead bin, a restraint device, a spacesuit, a door, a vacuum door, a steering wheel, or a diving suit.

* * * * *